United States Patent [19]

Shaw

[11] E Re. 29,088

[45] Reissued Dec. 28, 1976

[54] SURGICAL CUTTING INSTRUMENT HAVING ELECTRICALLY HEATED CUTTING EDGE

[76] Inventor: Robert F. Shaw, 135 Willow Brook Drive, Portola Valley, Calif. 94025

[22] Filed: Oct. 28, 1975

[21] Appl. No.: 625,845

Related U.S. Patent Documents

Reissue of:

[64] Patent No.: 3,768,482
Issued: Oct. 30, 1973
Appl. No.: 295,879
Filed: Oct. 10, 1972

U.S. Applications:

[63] Continuation of Ser. No. 63,645, Aug. 13, 1970, abandoned, which is a continuation of Ser. No. 681,737, Nov. 9, 1967, abandoned.

[52] U.S. Cl. ..... 128/303.17; 30/140; 128/303.14

[51] Int. Cl.[2] ..... A61B 17/32; A61N 3/00

[58] Field of Search ..... 128/303.1, 303.14, 303.17; 30/140; 219/233, 242

[56] References Cited

UNITED STATES PATENTS

| | | | |
|---|---|---|---|
| 1,735,271 | 11/1929 | Groff | 128/303.14 |
| 1,794,296 | 2/1931 | Hyams | 128/303.14 |
| 1,930,214 | 10/1933 | Wappler | 128/303.14 |
| 2,012,938 | 9/1935 | Beuoy | 128/303.14 |
| 2,917,614 | 12/1959 | Caliri et al. | 128/303.1 X |
| 3,234,356 | 2/1966 | Babb | 128/303.1 |
| 3,526,750 | 9/1970 | Siegel | 219/233 |
| 3,584,190 | 6/1971 | Marcoux | 219/233 |
| 3,648,001 | 3/1972 | Anderson | 128/303.14 X |
| 3,662,755 | 5/1972 | Rautenbach | 128/303.1 |
| 3,826,263 | 7/1974 | Cage | 128/303.1 |

*Primary Examiner*—Aldrich F. Medbery
*Attorney, Agent, or Firm*—Lyon & Lyon

[57] ABSTRACT

A surgical cutting instrument includes an electrically heated cutting edge and a power supply system for maintaining the cutting edge at a constant high temperature for sterilizing the blade, cutting tissue, and cauterizing the incised tissue to reduce hemorrhage from the cut surfaces of the tissues (hemostasis).

13 Claims, 3 Drawing Figures

SURGICAL CUTTING INSTRUMENT HAVING ELECTRICALLY HEATED CUTTING EDGE

Matter enclosed in heavy brackets [ ] appears in the original patent but forms no part of this reissue specification; matter printed in italics indicates the additions made by reissue.

*RELATED APPLICATION*

*This application is a reissue of Pat. 3,768,482 which matured from application 295,879 filed October 10, 1972 and which is a continuation of continuation-in-part of U.S. Pat. Application Ser. No. 63,645 filed August 13, 1970, now abandoned, which is a continuation of U.S. Pat. Application Ser. No. 681,737 filed Nov. 9, 1967, now abandoned.*

The control of bleeding during surgery accounts for a major portion of the total time involved in an operation. The bleeding that occurs when tissue is incised obscures the surgeon's vision, reduces his precision and often dictates slow and elaborate procedures in surgical operations. Each bleeding vessel must be grasped in pincer-like clamps to stop the flow of blood and the tissue and vessel within each clamp must then be tied with pieces of fine thread. These ligated masses of tissue die and decompose and thus tend to retard healing and promote infection.

SUMMARY OF THE INVENTION

Accordingly, the present invention provides a surgical cutting instrument having a cutting edge which is electrically heated to a constant high temperature for sterilizing the blade, cutting the tissue and cauterizing the surfaces of the incision, thereby allowing surgery to be more rapidly performed. This is accomplished in accordance with the illustrated embodiment of this invention by providing electrically heated elements disposed to form the cutting edge of the blade and by providing a common constant voltage source which operates to maintain the cutting edge at a high substantially constant temperature during its use. The hot cutting edge according to the present invention decreases the amount of tissue that is damaged and reduces the tendency of the instrument to stick to the heated tissue in the incision. In one embodiment, the material used in the electrically heated cutting edge has a positive temperature coefficient of resistance. The temperature at which the cutting edge of the blade is maintained depends upon such factors as the nature of the tissue to be cut, the speed of cutting desired, the degree of tissue coagulation desired, and the non-adherence of the blade to the incised tissue and generally is maintained between 300°–1,000° Centigrade for typical incisions in typical human tissue. The cutting edge includes many parallel current paths in a conductive material connected between the terminals of a constant-voltage power source. The operating temperature of the cutting edge is controlled by altering the voltage between the terminals.

The handle of the cutting instrument is thermally insulated from the blade to permit comfortable use of the instrument and the handle and blade with its electrically-heated cutting edge are detachable for easy replacement and interchangeability with blades having cutting edges of various shapes and sizes determined by the nature of the incision to be made and the tissue to be cut.

DESCRIPTION OF THE PREFERRED EMBODIMENT

Figure 3:
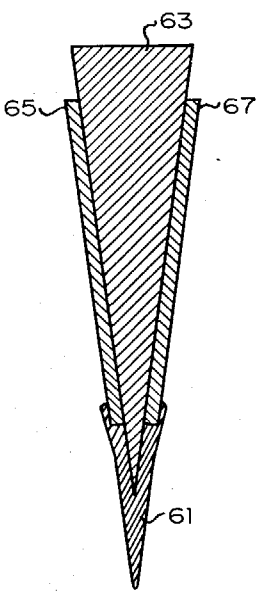
FIG. 3 is an end sectional view of the embodiment of FIG. 1 showing the heater element disposed as the cutting edge of the blade between electrodes on opposite sides thereof.
Figure 1:
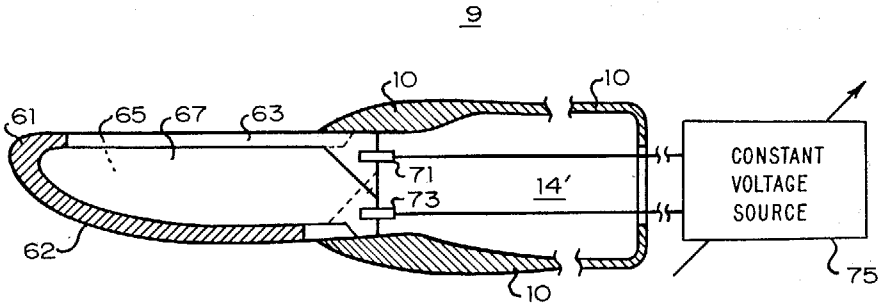
FIGS. 1 and 2 are pictorial views of embodiments of cutting instruments according to the present invention.

Referring now to FIGS. 1 and 3 of the drawing, there is shown the surgical cutting instrument 9 including a thin ceramic card 63 in the desired shape of a surgical cutting blade which is detachable from the handle or holder 10. An electrical heating element 61 is disposed in the region of, i.e. on or about, the cutting edge 62 of ceramic card 63 between electrodes 65 and 67 which are electrically connected to a constant voltage source through the cable 14 and the connectors 71 and 73. The element 61 may be a continuous conductive film attached to the card 63, for example, using conventional vapor-deposition processes. The material used for the element 61 may be tantalum nitride or other similar material having a positive temperature coefficient of resistance. Thus, as a portion of the element cools when in contact with tissue, the resistance of such portion of the element decreases and draws increased current from the constant voltage source 75. This localizes the portion of the element 61 in which additional power is dissipated to the portion cooled on contact with tissue. The temperature of such portions of the element may thus be maintained substantially constant as the cutting edge comes in contact with tissue being cut. Other suitable materials having positive temperature coefficients of resistance for use as the element 61 include tungsten, nickel, platinum, chromium, alloys of such metals, and the like.

Figure 2:
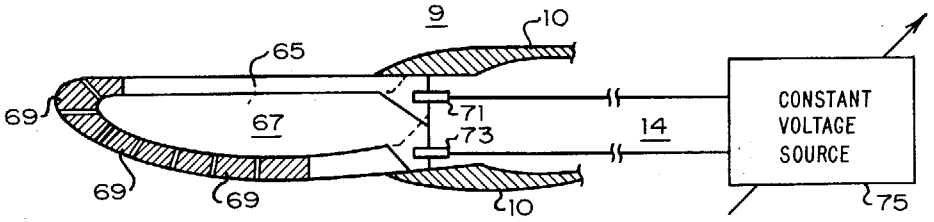

In the embodiment of the present invention illustrated in FIGS. 1 and 3, the heating element 61 is laterally disposed across the cutting edge 62 of the blade-like support card 63 to form a continuum of current-conducting paths along the length of the cutting edge. These current-conducting paths of heating element 61 are all parallel-connected between the contact electrodes 65 and 67 and which are disposed on opposite sides of the support card 63. These contact electrodes may be formed of a material such as platinum or tungsten, or the like, which makes good contact with the heating element material and which does not readily oxidize at elevated operating temperatures. Alternatively, the heating element 61 may also be arranged to traverse the cutting edge 62 as discrete, closely-spaced elements 69 that are all parallel-connected between opposite-side electrodes 65 and 67 on the card 63, as shown in FIG. 2. Such discrete elements are connected on one side of the card 63 to the electrode 67 and on the other side of the card to electrode 65. In the limit, the heating elements 69, as shown in FIG. 2, may be sufficiently closely located along the cutting edge 62 in parallel connection between the opposite-side electrodes 65 and 67, as to perform substantially as a continuous conductive film, as shown in FIG. 1.

In each of the illustrated embodiments, the electrodes 65 and 67 and heating elements 61 or 69 may be conductive material which is vapor-deposited in the desired interconnected patterns on a suitable electrically-insulating ceramic card 63. Alternatively, the electrodes and heater elements may be etched to shape on a card 63 whose side surfaces and edges are coated with the selected conductive materials.

In each of these embodiments, the electrodes 65, 67 are connected through conductors 14 and suitable electrical connectors 71, 73 mounted in the handle 10 to a source 75 of substantially constant voltage. This source 75 may be a conventional, well-regulated power supply or other low-output impedance supply which is capable of delivering the total current required by all portions of heating element 61 (or by all discrete elements 69) while maintaining the voltage between electrodes 65 and 67 substantially constant. In this way, each portion of heating element 61 (or discrete element 69) which cools down when placed in contact with tissue during surgical use decreases in resistance between electrodes (for positive temperature coefficient of resistance). With constant voltage applied to the electrodes, the cooled regions draw correspondingly more current and dissipate more power in the cooled region, thereby tending to maintain the heating element all along the cutting edge at the preselected operating temperature. The operating temperature of the cutting edge is thus selected by altering the value of the constant voltage supplied by source 75. To assure substantially uniform operating temperature over the length of the cutting edge 62, the heating element 61 (or the discrete elements 69 closely spaced about the edge) may have substantially uniform resistance per unit area. The ceramic card 63 may be formed of high thermal conductivity material such as aluminum oxide, or the like, to assure more uniform operating temperature along the length of the cutting edge.

I claim:

1. A surgical instrument for cutting tissue with simultaneous hemostasis, the instrument comprising:

insulating support means having *as a portion thereof* a tissue-cutting edge [and including thereon] *region and including in physical contact with said support means* an electrically-heatable element of electrically-conductive material disposed on said edge region defining a cutting edge to contact tissue and to conduct electrical current along a plurality of parallel current paths for directly heating the cutting edge in response to electrical signal applied thereto; and connection means on said instrument providing electrical connections to said element for supplying electrical signal thereto to be conducted along a plurality of parallel current paths.

2. A surgical instrument as in claim 1 wherein said electrically-heatable element includes a substantially continuous conductive layer disposed adjacent the cutting edge; and said connection means includes a pair of electrodes which are disposed in spaced relationship on opposite sides of said support means and which are connected to said conductive layer on opposite sides of the cutting edge for conducting current along a plurality of parallel current paths oriented substantially laterally across the cutting edge.

3. A surgical instrument as in claim 1 wherein:

[said] electrodes are disposed on opposite sides of said support means; and the electrically-heatable element includes a plurality of discrete electrically-heatable elements disposed to traverse the cutting edge [of said support means] and connected at the ends thereof to electrodes on opposite sides of said support means.

4. A surgical instrument as in claim 1 wherein:

said electrically-heatable element on said support means is formed of electrically-conductive material which has positive-temperature coefficient of resistance; and said connection means includes a source of substantially constant voltage connected to [said pair of] electrodes for maintaining the voltage across the element substantially constant as portions of said element contact tissue.

*5. A hemostatic surgical cutting blade comprising:*

*a cutting blade having a tissue cutting edge;*

*an electrically heatable element of electrically conductive material thermally connected to and at least extending along the area of the cutting edge such that said edge may be maintained within a predetermined temperature range; and*

*two or more electrodes disposed in spaced relationship on the cutting blade and connected to said electrically conductive material for conducting current along a plurality of parallel current paths.*

*6. The hemostatic surgical cutting blade claimed in claim 5 wherein said electrodes are disposd in lateral spacial relationship on opposite sides of said cutting edge for conducting current along a plurality of parallel current paths oriented substantially laterally across the cutting edge.*

*7. The hemostatic surgical cutting blade claimed in claim 5 wherein said electrically heatable element is further defined as comprising a plurality of discrete electrically heatable elements.*

*8. The hemostatic surgical cutting blade claimed in claim 5 wherein said electrically heatable element is formed from a material having a positive-temperature coefficient.*

*9. The method of cutting tissue with simultaneous hemostasis comprising the steps of:*

*contacting the tissue to be cut with a tissue cutting edge at an elevated temperature;*

*establishing the elevated temperature by conducting current along a plurality of substantially parallel current paths located along said tissue cutting edge; and*

*increasing power dissipation in regions of the edge which are selectively cooled upon contact with tissue for maintaining the temperature of the edge within a selected range.*

*10. A method of cutting tissue with simultaneous hemostasis comprising:*

*conducting current along a plurality of substantially parallel current paths oriented laterally across a supported tissue cutting edge;*

*dissipating power in regions of said tissue cutting edge responsive to selective cooling of said regions by reason of contact with tissue; thereby maintaining said tissue cutting edge at a selected temperature range.*

*11. A method of hemostatic surgery as in claim 9 wherein:*

*current is conducted along a plurality of substantially parallel current paths which are discrete.*

*12. A method of hemostatic surgery according to claim 9 wherein:*

*the resistance of the parallel current paths increases with increasing temperature thereof.*

*13. A method of hemostatic surgery according to claim 12 wherein:*

*a constant voltage is impressed upon the current paths.*

* * * * *